United States Patent
Amundson et al.

(10) Patent No.: US 7,110,824 B2
(45) Date of Patent: Sep. 19, 2006

(54) ADAPTIVE TELEMETRY SYSTEM AND METHOD FOR AN IMPLANTABLE MEDICAL DEVICE

(75) Inventors: Mark D. Amundson, Cambridge, MN (US); William J. Linder, Golden Valley, MN (US); Karen M. Lent, Stillwater, MN (US); Scott T. Mazar, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 347 days.

(21) Appl. No.: 10/638,945

(22) Filed: Aug. 11, 2003

(65) Prior Publication Data

US 2004/0127959 A1 Jul. 1, 2004

Related U.S. Application Data

(62) Division of application No. 09/900,717, filed on Jul. 6, 2001, now abandoned.

(51) Int. Cl.
*A61B 5/07* (2006.01)
*A61N 1/08* (2006.01)
(52) U.S. Cl. .................. 607/60; 600/302; 128/903

(58) Field of Classification Search .............. 600/302; 120/903; 607/32, 60
See application file for complete search history.

(56) References Cited

U.S. PATENT DOCUMENTS

| 4,304,237 A | 12/1981 | Mensink |
| 4,562,841 A | 1/1986 | Brockway et al. |
| 4,625,730 A | 12/1986 | Fountain et al. |
| 5,342,408 A | 8/1994 | deCoriolis et al. |
| 5,466,246 A | 11/1995 | Silvian |
| 5,683,432 A | 11/1997 | Goedeke et al. |
| 6,400,990 B1 | 6/2002 | Silvian |
| 6,443,891 B1 * | 9/2002 | Grevious ............... 600/302 |

* cited by examiner

*Primary Examiner*—Scott M. Getzow
(74) *Attorney, Agent, or Firm*—Schwegman, Lundberg, Woessner & Kluth, P.A.

(57) ABSTRACT

A system and method for transmitting telemetry data from an implantable medical device to an external device. A connection-oriented protocol is used to transmit data at a higher data rate while a burst mode protocol is used to transmit data a lower data rate. The lower data rate may be used for remote communications where the received signal is of lower power.

14 Claims, 3 Drawing Sheets

ADAPTIVE TELEMETRY SYSTEM AND METHOD FOR AN IMPLANTABLE MEDICAL DEVICE

CROSS-REFERENCE TO RELATED APPLICATION(S)

This application is a division of U.S. patent application Ser. No. 09/900,717, filed on Jul. 6, 2001, now abandoned, the specification of which is incorporated herein by reference.

FIELD OF THE INVENTION

This invention pertains to implantable medical devices such as cardiac pacemakers and implantable cardioverter/defibrillators. In particular, the invention relates to a system and method for transmitting telemetry data from such devices.

BACKGROUND

Implantable medical devices, including cardiac rhythm management devices such as pacemakers and implantable cardioverter/defibrillators, typically have the capability to communicate data with an external device called an external programmer via a radio-frequency telemetry link. One use of such an external programmer is to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations. External devices for remote monitoring may also receive telemetry data from an implantable device where, for the convenience of the patient, the communications must take place over greater distances than with the typical external programmer.

SUMMARY OF THE INVENTION

The present invention is a system and method for optimizing short and long-range telemetry communications between an implantable medical device and an external device such as an external programmer or remote monitor. In accordance with the invention, data is transmitted from the implantable device to the external device at either a higher or lower data rate. A connection-oriented protocol is used to transmit data at the higher rate, while a connectionless burst mode protocol is used to transmit data at the lower rate. The lower data rate signal has a narrower bandwidth than the higher data rate signal permitting the use of a narrower bandpass filter at the receiver to lower the noise floor. The higher data rate may be used to advantage where transmission distances are short, while the lower data rate signal is most useful for more remote communications where the signal-to-noise ratio is lower. The use of the a burst mode communications protocol lowers the overhead inefficiencies associated with non-message data and improves the rate at which message data is transmitted at the lower data rate.

DETAILED DESCRIPTION

Figure 1:
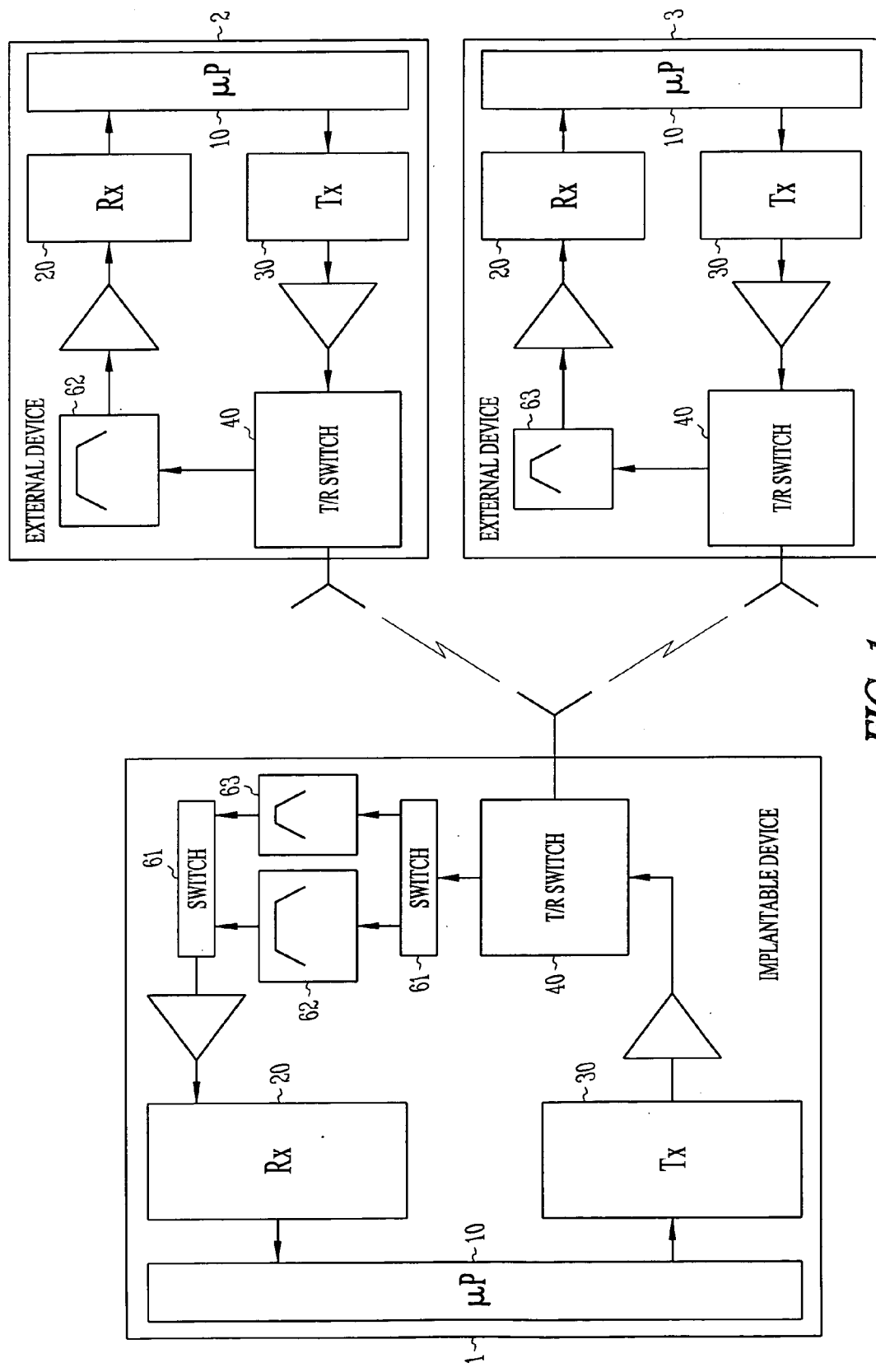
FIG. 1 is a block diagram of an exemplary telemetry system for an implantable medical device.

Telemetry systems for implantable medical devices utilize radio-frequency energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is hereby incorporated by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand that can be positioned in proximity to the implanted device. The implantable device generates and receives the radio signal by means of an antenna, such as may be formed by a wire coil wrapped around the periphery of the inside of the device casing. Other types of telemetry systems may utilize far-field electromagnetic radiation or other types of data links such as telephone lines to enable communications over greater distances. Such long-range telemetry may be useful in applications where the implantable device transmits data to a remote monitoring unit or other external device. The present invention is concerned with efficiently enabling both types of communications.

The limited energy storage capability of typical implantable medical devices such as those used for cardiac rhythm management necessitates that the signals transmitted from the implantable device be of relatively low energy, thus decreasing the signal-to-noise ratio of the signal received by the external programmer or other external device. The signal-to-noise ratio is even lower when telemetry is performed over longer distances owing to the attenuation of the transmitted signal. In accordance with the present invention, data is transmitted from the implantable device to an external device at either a higher or lower data rate, where the data rate refers to the total rate at which both message data and protocol data is transmitted. Message data is the information that is actually desired to be conveyed to the external device, while protocol data is the overhead associated with implementing the communications protocol, including data used for error detection and correction. As explained below, using different data rates allows the telemetry to be optimized for the transmission distance involved or for noisy conditions.

The data transmitted by the implantable device is digital data that can be transmitted directly as baseband data in certain types of data links but is more typically used to modulate a carrier signal. In either case, the data is transmitted in the form of symbols representing one or more bits of information. For example, in on-off amplitude shift keying, each pulse represents either a one or a zero. Other modulation methods (e.g., M-ary modulation techniques) utilize symbols representing a greater number of bits. The minimum bandwidth of a signal transmitting B symbols per second is ½ B Hz according to the Nyquist sampling theorem. An optimally transmitted lower symbol rate signal therefore has a narrower bandwidth than an optimally transmitted higher symbol rate signal. The lower data rate signal transmitted by the implantable medical device can thus be transmitted with a lower symbol rate and narrower bandwidth than the high data rate signal.

At the receiver of the external device, a bandpass filter centered about the frequency of the carrier signal can be used to remove broadband noise from the received signal and improve the signal-to-noise ratio by lowering the noise floor. The higher the data rate of the signal, the wider the passband needs to be in order to accommodate the bandwidth of the transmitted signal. A wide passband is less effective in removing broadband noise, but this may be satisfactory if the signal strength is adequate. When transmitting data over long distances or under otherwise suboptimal conditions, however, the noise floor may be such that wide passband filtering does not remove enough noise to allow satisfactory communications. In accordance with the present invention, a lower data rate signal is then used. Because a lower data rate signal has a lower bandwidth than a higher data rate signal, a bandpass filter with a narrower passband may be used by the receiver for the lower data rate signal to further lower the noise floor and boost the signal-to-noise ratio. The lower data rate signal, as compared with the higher data rate signal, is thus useful for transmitting data over long distances to a remotely located external device where significant attenuation of the signal occurs or for transmitting data in noisy environments. The higher data rate signal, on the other hand, can advantageously be used when transmission conditions are optimum such as when a wand of an external programmer is placed in close proximity to the implantable device.

FIG. 1 is a block diagram of the telemetry components of an implantable medical device 1 and two representative external devices 2 and 3. Each of the devices has a microprocessor or other type of controller 10 for processing the digital data. Software or firmware executed by the controller implements the communications protocols described above when transmitting or receiving messages. A data receiver 20 and a data transmitter 30 are interfaced to the controller in each of the devices for receiving and transmitting a modulated carrier signal. The carrier signal is typically a radio-frequency signal transmitted wirelessly as shown in the figure but could also be signal transmitted over another medium such as a phone line. A demodulator for extracting digital data from the carrier signal is incorporated into each receiver, and a modulator is incorporated into each transmitter for modulating the carrier signal with digital data. Signals received from the antenna 50 are routed by a transmit/receive switch 40 to the receiver 20 through a bandpass filter 61 or 62 and an amplifier. Modulated carrier signals from transmitter 30 are fed to an amplifier and routed to the antenna 50 by transmit/receive switch 40.

The external device 2 is meant to represent a device designed for close-range telemetry such as an external programmer where the antenna 50 is incorporated into a wand for positioning close to the implantable device. Data communications would therefore preferably take place at the higher data rate, and the receive bandpass filter 62 is a wide passband filter to accommodate the bandwidth of the received signal. The external device 3 is intended to represent a remote monitoring unit designed for long-range communications at the lower data rate. The receive bandpass filter 63 accordingly has a narrower passband for removing as much broadband noise as possible. Different external devices, such as external devices 2 and 3, may be designed to receive data in a manner optimized for different conditions. The implantable device 1, however, must be able to adaptively communicate at either the higher or lower data rate. The implantable device therefore has a pair of bandpass filters 63 and 62 with narrow and wide passbands, respectively. A bandwidth switch 61 switches the signal path from one filter to the other.

As aforesaid, both message data and protocol data are transmitted by the implantable device. In order to improve the rate at which message data is transmitted at the lower data rate, the present invention uses different communications protocols for the lower and higher data rates. A communications protocol is a set of rules that specify the format of messages and the appropriate actions required for each message. Communications protocols for implementing biomedical telemetry between devices are similar to the protocols used in computer networks. In such protocols, message data to be transferred from one device to another is organized into packets to which are then encapsulated with protocol data (i.e., bits added to the beginning and/or end of the packet) that facilitates the transfer of the message data to and from different software components in each device. Most computer communications protocols can be conceptualized in accordance with a layering model in which the functions that need to be performed by the protocol are divided into subprotocols, called layers. For example, the well-known internet protocol suite TCP/IP has five layers, with the most fundamental being the physical layer corresponding to the physical hardware used to effect communications over the network. In the biomedical telemetry context, the physical layer is the modulation/demodulation and transmitter/receiver circuitry used to transmit digital data through free space or over another medium. The remaining layers of the internet protocol suite correspond to software components that use the hardware. Each time a layer processes a message packet for transmission, encapsulation bits associated with that layer are added to the packet. The secondary layer is the framing layer (a.k.a., network interface or data link layer) that organizes the data (message data and other protocol data) into frames that can be transmitted using the physical layer. Framing of the packet includes adding bits to signify where a frame starts and for error detection/correction. Another layer is the transport layer that specifies how to enable reliable transfer of data such that transmitted data is guaranteed to be received. Different layers of the protocol can be used to produce different protocols that perform with different functionalities. As described below, the subprotocols can be used in a biomedical telemetry system to adaptively optimize the communications protocol to the particular data rate being used.

Figure 2:
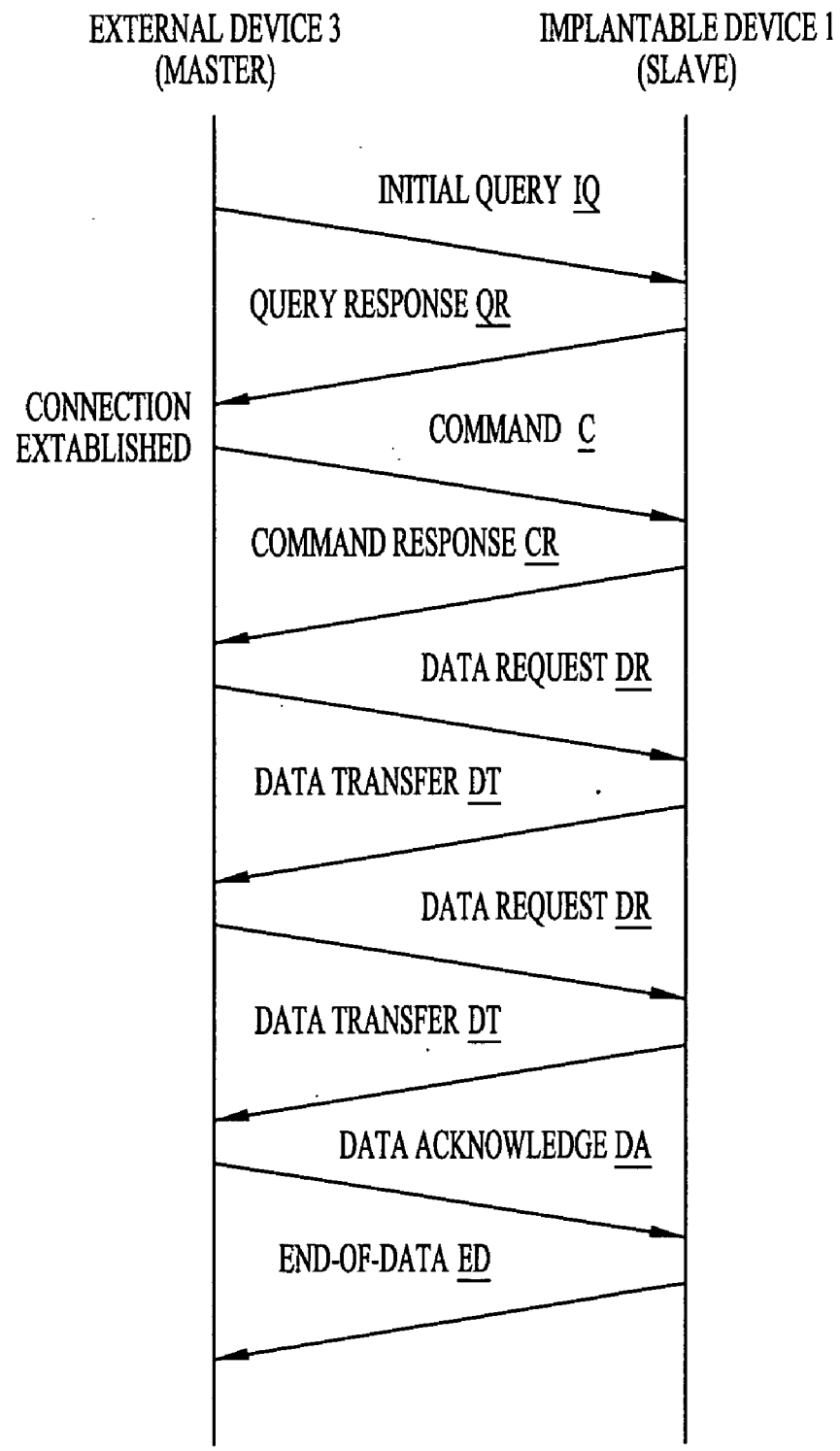
FIG. 2 illustrates an exemplary connection-oriented telemetry protocol.

In accordance with the invention, a connection-oriented protocol where a data transfer is initiated by a request from either the implantable device or the external device is used to transmit data at the higher rate. The protocol may also include provision for reliably transferring data such that transmitted data is acknowledged by the recipient when the data is received and retransmitted by the sender if the data is unacknowledged. Such a protocol is similar to TCP (transmission control protocol), which is the protocol used on the world wide web and is implemented via the transport layer of the internet protocol suite. In an exemplary implementation of a connection-oriented protocol, illustrated as a packet flow diagram in FIG. 2, the implantable device 1 and the external device 2 communicate with the protocol in a master/slave relationship. Starting at the top of the diagram, the external device 2 issues an initial query IQ that is successfully recognized by the implantable device 1. A query response QR is then sent to the implantable device, and the connection between the two devices is established. The external device then issues commands C or data requests DR to the implantable device which responds with command responses CR or data transfers DT, respectively. Upon receipt of data DT by the external device, a data acknowledgement DA is sent to the implantable device. To ensure reliable transfer of the data, if no data acknowledgement DA is received by the implantable device for a data transfer DT, the data is retransmitted. The connection is terminated after the implantable device sends an end-of-data signal ED.

Figure 3:
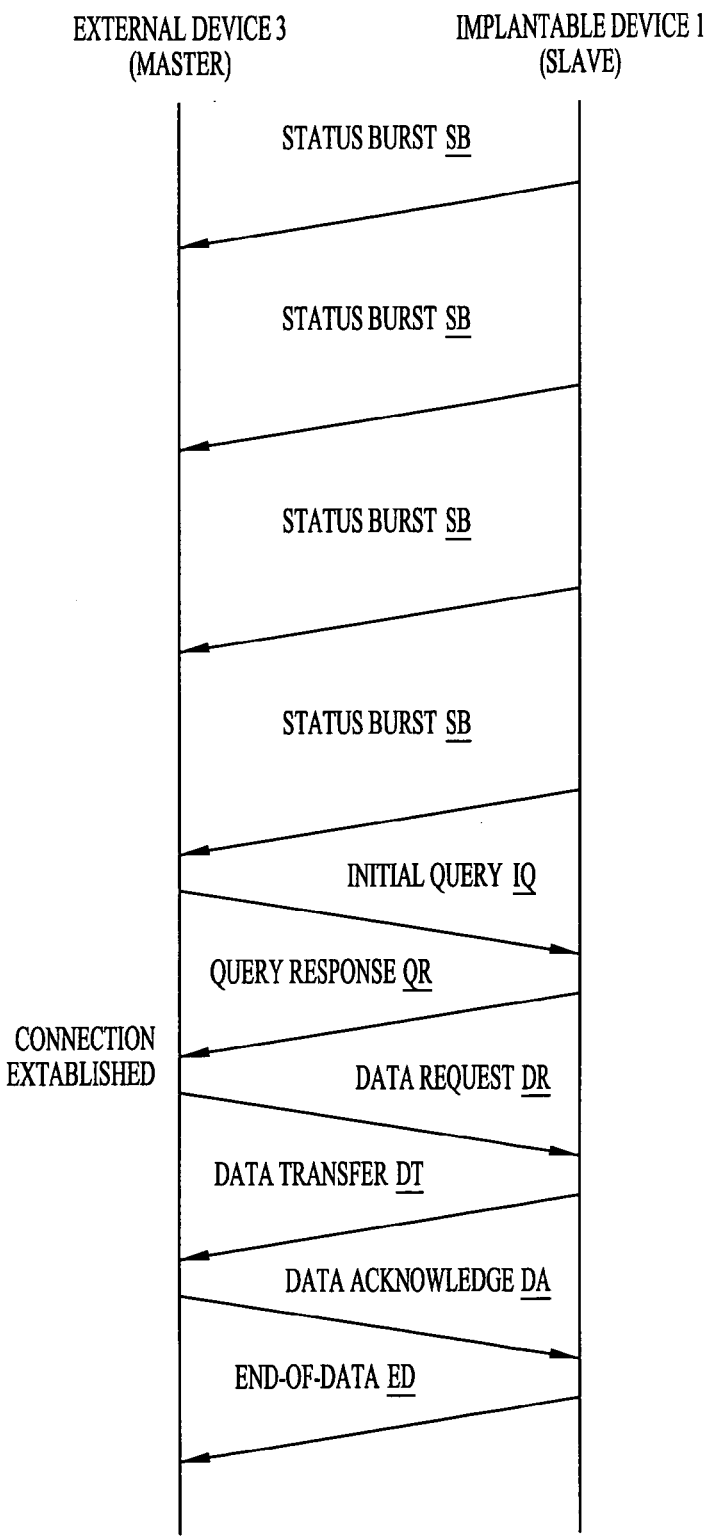
FIG. 3 illustrates an exemplary burst mode protocol.

In order to improve the efficiency of message data transfer, a connectionless or burst mode protocol is used to transmit data at the lower data rate. A connectionless protocol would normally use only the framing layer of the protocol suite such that data is encapsulated with framing bits and sent autonomously (i.e., in bursts). There is thus no need for a data request by the recipient, and there is also no provision for data acknowledgement by the recipient. By eliminating the overhead associated with providing a connection-oriented service or providing reliable transfer of data, the use of the burst mode telemetry protocol improves the rate at which message data is transmitted at the lower data rate. FIG. 3 illustrates an exemplary implementation of a connectionless or burst mode protocol. The implantable device 1 autonomously sends status bursts SB containing data relating to the status of the device or the patient. The status bursts may be sent periodically or upon detection of some event or other change in status. If the external device 3 receives a status burst indicating a change in status, it may establish a connection similar to that illustrated in FIG. 2 with an initial query IQ that the implantable device responds to with a query response QR. The two devices then exchange data requests DR, data transfers DT, and data acknowledgements DA until the implantable device sends an end-of-data ED. Thus, use of the connection-oriented or master/slave protocol is not precluded at the lower data rate, but preferable use of the connectionless protocol may at least minimize such data requests even if the implantable device status bursts do not contain enough information to satisfy the external device. A connection-oriented protocol could also be used at the lower data rate to initiate a data transfer session with the connectionless protocol.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for transmitting telemetry data from an implantable medical device, comprising:
   transmitting data from the implantable device to an external device at either a higher or lower data rate;
   wherein data is transmitted at the lower rate using a burst mode telemetry protocol, wherein the burst mode telemetry protocol dictates that transmitted data packets are sent autonomously with no provision for data acknowledgement; and,
   wherein data is transmitted at the higher rate using a connection-oriented telemetry protocol, wherein the connection-oriented telemetry protocol dictates that transmitted data packets are acknowledged by the external device and retransmitted if the transmitted data packets are unacknowledged.

2. The method of claim 1 wherein data is transmitted at the lower rate with a lower symbol rate and narrower bandwidth than at the high rate.

3. The method of claim 2 further comprising receiving the modulated carrier signal at the external device and bandpass filtering the signal with a wider or narrower passband depending upon whether the signal contains data transmitted at the higher or lower rate, respectively.

4. The method of claim 1 wherein data is transmitted to the external device by modulating a radio-frequency carrier signal.

5. The method of claim 1 further comprising transmitting data at the lower rate upon a request for data transmission at that rate from the external device.

6. The method of claim 1 wherein the connection-oriented protocol is a master/slave protocol in which communications are initiated by a data request from the external device to the implantable medical device.

7. The method of claim 1 wherein data is transmitted at the higher rate when the implantable device and external device are in close proximity.

8. The method of claim 1 wherein data is transmitted at the lower rate when transmission conditions are noisy.

9. A system for transmitting telemetry data from an implantable medical device, comprising:
   means for transmitting data from the implantable device to an external device at either a higher or lower data rate;
   wherein data is transmitted at the lower rate using a burst mode telemetry protocol, wherein the burst mode telemetry protocol dictates that transmitted data packets are sent autonomously with no provision for data acknowledgement; and,
   wherein data is transmitted at the higher rate using a connection-oriented telemetry protocol, wherein the connection-oriented telemetry protocol dictates that transmitted data packets are acknowledged by the external device and retransmitted if the transmitted data packets are unacknowledged.

10. The system of claim 9 wherein data is transmitted at the lower rate with a lower symbol rate and narrower bandwidth than at the high rate.

11. The system of claim 10 further comprising means for receiving the modulated cater signal at the external device and means for bandpass filtering the signal with a wider or narrower passband depending upon whether the signal contains data transmitted at the higher or lower rate, respectively.

12. The system of claim 9 wherein data is transmitted to the external device by modulating a radio-frequency cater signal.

13. The system of claim 9 further comprising means for transmitting data at the lower rate upon a request for data transmission at that rate from the external device.

14. The system of claim 9 wherein the connection-oriented protocol is a master/slave protocol in which communications are initiated by a data request from the external device to the implantable medical device.

* * * * *

UNITED STATES PATENT AND TRADEMARK OFFICE
CERTIFICATE OF CORRECTION

PATENT NO. : 7,110,824 B2 Page 1 of 1
APPLICATION NO. : 10/638945
DATED : September 19, 2006
INVENTOR(S) : Amundson et al.

It is certified that error appears in the above-identified patent and that said Letters Patent is hereby corrected as shown below:

In column 6, line 47, in Claim 11, delete "cater" and insert -- carrier --, therefor.

In column 6, line 53, in Claim 12, delete "cater" and insert -- carrier --, therefor.

Signed and Sealed this

Twenty-sixth Day of December, 2006

JON W. DUDAS
*Director of the United States Patent and Trademark Office*